(12) United States Patent
Furuki et al.

(10) Patent No.: US 8,553,229 B2
(45) Date of Patent: Oct. 8, 2013

(54) FINE PARTICLE OPTICAL MEASURING METHOD IN FLUIDIC CHANNELS

(75) Inventors: Motohiro Furuki, Tokyo (JP); Shingo Imanishi, Kanagawa (JP); Masataka Shinoda, Tokyo (JP); Akitoshi Suzuki, Shizuoka (JP); Kazushi Miyake, Tokyo (JP)

(73) Assignee: Sony Corporation, Tokyo (JP)

( * ) Notice: Subject to any disclaimer, the term of this patent is extended or adjusted under 35 U.S.C. 154(b) by 558 days.

(21) Appl. No.: 12/259,235

(22) Filed: Oct. 27, 2008

(65) Prior Publication Data

US 2009/0116005 A1    May 7, 2009

(30) Foreign Application Priority Data

Nov. 2, 2007    (JP) ................ P2007-285671

(51) Int. Cl.
*G01N 35/08*    (2006.01)
*G01N 21/05*    (2006.01)

(52) U.S. Cl.
USPC ............... 356/440; 356/436; 422/82.09

(58) Field of Classification Search
USPC .......... 356/335–343, 409–415, 436, 441–442
See application file for complete search history.

(56) References Cited

U.S. PATENT DOCUMENTS

| | | | | |
|---|---|---|---|---|
| 5,112,134 A | * | 5/1992 | Chow et al. | 356/427 |
| 2008/0186488 A1 | * | 8/2008 | Kiesel et al. | 356/335 |
| 2009/0101847 A1 | * | 4/2009 | Furuki et al. | 250/492.1 |

FOREIGN PATENT DOCUMENTS

| | | |
|---|---|---|
| JP | 57-060248 | 4/1982 |
| JP | 2001-264232 | 9/2001 |
| JP | 2004-301733 | 10/2004 |

OTHER PUBLICATIONS

Office Action from the Japanese Patent Office for Japanese Patent Application No. JP-2007-285671, (Sep. 24, 2009).

* cited by examiner

*Primary Examiner* — Gregory J Toatley
*Assistant Examiner* — Rebecca C Bryant
(74) *Attorney, Agent, or Firm* — Finnegan, Henderson, Farabow, Garrett & Dunner LLP

(57) ABSTRACT

A fine particle measuring method of performing optical measurement of fine particles introduced into a plurality of sample fluidic channels provided at predetermined distances on a substrate by scanning light to the sample fluidic channels is disclosed. The method includes: sequentially irradiating the light to at least two or more reference regions provided together with the sample fluidic channels; detecting a change of optical property occurring in the light due to the reference regions; and controlling timing of emission of the light to the sample fluidic channels.

3 Claims, 5 Drawing Sheets

FINE PARTICLE OPTICAL MEASURING METHOD IN FLUIDIC CHANNELS

CROSS REFERENCES TO RELATED APPLICATIONS

The present invention contains subject matter related to Japanese Patent Application JP 2007-285671 filed in the Japanese Patent Office on Nov. 2, 2007, the entire contents of which being incorporated herein by reference.

BACKGROUND OF THE INVENTION

1. Field of the Invention

The present invention relates to a fine particle measuring method, a substrate for fine particle measurement, and a fine particle measuring apparatus. More specifically, the present invention relates to a fine particle measuring method capable of controlling the timing of emission of light to sample fluidic channels into which fine particles are introduced.

2. Description of the Related Art

In order to distinguish fine particles, such as biological fine particles including cells, microorganisms, and liposomes, or synthetic particles including latex particles, gel particles, and industrial particles, apparatuses that introduce fine-particle-dispersed liquid into fluidic channels and optically measure the fine particles introduced into the fluidic channels have been used in the related art.

As an example, there is a particle analyzer that distinguishes synthetic particles according to the size or shape. The particle analyzer measures the element composition or diameter of a fine particle and the number of particles by exciting and emitting fine particles in helium (He) plasma one by one to perform spectral detection of the fine particles.

Moreover, for the biological fine particles, optical measurement using flow cytometry (flow cytometer) is widely performed. The flow cytometry is a technique of measuring the size or structure of a fine particle to be measured, such as a cell or a microbead, by making the fine particle flow to the middle of laminar flow of sheath liquid in a flow cell, irradiating light onto the fine particle by means of an optical detection unit, and detecting scattered light or fluorescence generated from the fine particle.

In recent years, a microchip for performing such optical measurement of a fine particle within a fluidic channel provided on a substrate formed of glass or plastics by using fine processing technology in a semiconductor industry is under development.

An analysis system using such a microchip is called a μ-TAS (micro-total-analysis system), a lab on chip, or a bio-chip and has been drawing attention as a technique of enabling an improvement in the speed of optical measurement of a fine particle, integration, or miniaturization of a measuring apparatus. In the case of the μ-TAS, applications to biological analysis of a precious micro sample or many samples are particularly expected since an analysis using a small amount of samples is possible or disposable use of a microchip is possible.

JP-T-2005-538727 discloses a microchip (refer to a particle sorting system 1700 of FIG. 17 in the document) for performing optical measurement and sorting of fine particles in fluidic channels. The particle sorting system 1700 includes a plurality of sorting modules 1701 (sample fluidic channels) operating in parallel. In the particle sorting system 1700, a sample is introduced from an input region 1710 into each sorting module 1701 and predetermined characteristics of particles are measured simultaneously in a detection region 1720. Thus, high-speed measurement and sorting of particles are realized.

SUMMARY OF THE INVENTION

In the case where a plurality of sample fluidic channels are provided on a substrate and optical measurement of fine particles are performed simultaneously like the microchip disclosed in JP-T-2005-538727, it is thought effective to scan and irradiate light for measurement to each sample fluidic channel.

In case of performing measurement by irradiating light to each sample fluidic channel separately and independently, a light source and an optical system for guiding light from the light source to the sample fluidic channel are needed for each sample fluidic channel. In contrast, the measurement can be performed with a single light source and a single optical system by scanning and irradiating light to a plurality of sample fluidic channels. In this case, since the configuration of an apparatus becomes simplified, the manufacturing cost of the apparatus can be suppressed.

Therefore, it is desirable to provide a measuring method, a substrate for measurement, and a measuring apparatus capable of obtaining high measurement accuracy when optical measurement of fine particles introduced into a plurality of sample fluidic channels provided on a substrate is performed by scanning light to the sample fluidic channels.

According to an embodiment of the present invention, a fine particle measuring method of performing optical measurement of fine particles introduced into a plurality of sample fluidic channels provided at predetermined distances on a substrate by scanning light to the sample fluidic channels includes the steps of: sequentially irradiating the light to at least two or more reference regions provided together with the sample fluidic channels; detecting a change of optical property occurring in the light due to the reference regions; and controlling timing of emission of the light to the sample fluidic channels.

In the fine particle measuring method, the timing of emission of the light to the sample fluidic channels is controlled on the basis of a time difference between a detection time of a change of the optical property caused by one of the reference regions and a detection time of a change of the optical property caused by another one of the reference regions and the number of sample fluidic channels.

In the fine particle measuring method, the reference regions may be reference fluidic channels into which fine particles for reference or/and a fluorescent material for reference are introduced. In this case, the timing of emission of the light to the sample fluidic channels may be controlled by detecting the change of the optical property caused by the fine particles for reference or/and the fluorescent material for reference.

Furthermore, according to another embodiment of the present invention, there is provided a substrate for fine particle measurement in which a plurality of sample fluidic channels are provided at predetermined distances and optical measurement of fine particles introduced into the sample fluidic channels is performed by scanning light to the sample fluidic channels includes at least two or more reference regions capable of causing a change of optical property of the light irradiated, the reference regions being provided together with the sample fluidic channels.

Furthermore, according to still another embodiment of the present invention, there is provided a fine particle measuring apparatus of performing optical measurement of fine particles introduced into a plurality of sample fluidic channels provided at predetermined distances on a substrate by scanning light to the sample fluidic channels including: a light irradiating section that sequentially irradiates the light to at least two or more reference regions provided together with the sample fluidic channels; a light detecting section that detects a change of optical property occurring in the light due to the reference regions; and a light control section that controls timing of emission of the light to the sample fluidic channels on the basis of an output from the light detecting section.

In the present invention, examples of the "fine particles" include various kinds of fine particles, such as biological fine particles including cells, microorganisms, and liposomes, or synthetic particles including latex particles, gel particles, and industrial particles. Examples of cells include an animal cell (for example, a blood cell) and a plant cell. Examples of microorganisms include bacteria such as a colon bacillus, viruses such as a tobacco mosaic virus, funguses such as yeast, and the like. Examples of biopolymer materials include a chromosome, a liposome, a mitochondrion, an organelle, and the like which form various cells. In addition, the industrial particles may be an organic polymer material, an inorganic polymer material, or metal, for example. Examples of organic polymer materials include polystyrene, styrene divinylbenzene, polymethylmethacrylate, and the like. Examples of inorganic polymer materials include glass, silica, a magnetic material, and the like. Examples of metal include gold colloid, aluminum, and the like. Generally, such fine particles have spherical shapes. However, the fine particles may have aspheric shapes. In addition, neither the size nor the mass is particularly limited.

In addition, it is assumed that the "reference region" means a region where light for optical measurement of fine particles is irradiated to cause a change in the optical property of the light. In addition, it is assumed that the "change of optical property" referred herein includes a wavelength change, a deflection change, and an intensity change caused by diffusion, diffraction, deflection, absorption, and the like of light. In a broad sense, it is assumed that the "change of optical property" further includes a change in which irradiated light is absorbed to emit fluorescent light with a different wavelength. Similarly, it is assumed that examples of the "fine particles for reference" and "fluorescent material for reference" include various kinds of materials causing such change of optical property of light.

According to the embodiments of the present invention, there are provided a measuring method, a substrate for measurement, and a measuring apparatus capable of obtaining high measurement accuracy when optical measurement of fine particles introduced into a plurality of sample fluidic channels provided on a substrate is performed by scanning light to the sample fluidic channels.

DESCRIPTION OF THE PREFERRED EMBODIMENTS

Hereinafter, a preferred embodiment of the present invention will be described with reference to the accompanying drawings. In addition, the embodiment described below is an example of a representative embodiment of the present invention but does not limit a range of the present invention.

Figure 1:
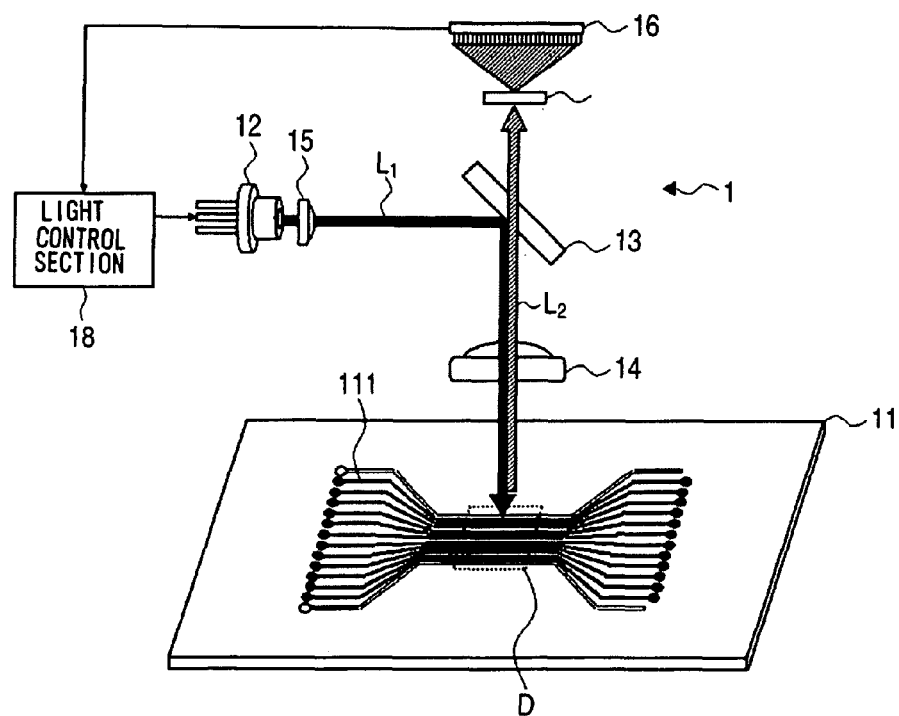
FIG. 1 is a schematic view illustrating the configuration of a fine particle measuring apparatus according to an embodiment of the present invention.

FIG. 1 is a schematic view illustrating the configuration of a fine particle measuring apparatus according to an embodiment of the present invention.

In the drawing, a fine particle measuring apparatus denoted by reference numeral 1 includes: a substrate 11 for fine particle measurement (hereinafter, simply referred to as a "substrate 11") in which sample fluidic channels 111, through which fine particles (samples) can be introduced, are provided; a laser light source 12 that emits laser light $L_1$ (refer to a black arrow in the drawing) for optical measurement of a fine particle; a scanning section 13 which scans the laser light $L_1$ to each sample fluidic channel 111 on the substrate 11, an objective lens 14 for condensing the laser light $L_1$ to a predetermined position of the sample fluidic channel 111; and a collimator lens 15 for making the laser light $L_1$ from the laser light source 12 into parallel beams.

A light detecting section including the laser light source 12, the scanning section 13, the objective lens 14, and the collimator lens 15 further includes a detector 16 for detecting light $L_2$ to be detected (refer to a hatched line arrow in the drawing), which is generated from fine particles introduced into the sample fluidic channel 111, by irradiating the measurement light $L_1$ to the sample fluidic channel 111.

The laser light $L_1$ (hereinafter, referred to as "measurement light $L_1$") is preferably used by selecting various wavelengths according to a fire particle to be measured and a purpose of measurement. As the laser light source 12, known light sources, such as gas lasers using argon, helium, and the like, a semiconductor laser (LD), and a light emitting diode (LED), may be properly selected and used.

For example, in order to measure the element composition of a fine particle, the measurement light $L_1$ having a wavelength corresponding to the absorption wavelength of each element is selected. In addition, in the case of measuring the fluorescence of fine particles marked with a plurality of fluorescent dye, the measurement light $L_1$ having a wavelength corresponding to the excitation wavelength of each fluorescent dye is used.

The scanning section 13 is disposed as a polygon mirror or a galvano mirror, an acousto-optic element, an electro-optic element, and the like on an optical path of the measurement light $L_1$ emitted from the laser light source 12 and scans the measurement light $L_1$ to the sample fluidic channel 111 at predetermined periods. For example, scanning may be performed at periods of about 1 kHz in the case of a dichroic mirror and about 20 kHz in the case of a tetracosahedral polygon mirror. Irradiation of the measurement light $L_1$ is preferably performed by a telecentric optical system in which the measurement light $L_1$ is irradiated vertically to the sample fluidic channel 111 and the spot width of the measurement light $L_1$ on an imaging surface on each sample fluidic channel 111 is fixed.

The detector 16 detects and amplifies the light to be detected $L_2$ generated from a fine particle, converts the light to be detected $L_2$ into an electric signal, and outputs light to be detected $L_2$ to an analysis section (not shown). The analysis section analyzes an optical property of the fine particle on the basis of the input electric signal and outputs the measurement result. In FIG. 1, a case of grating the light to be detected $L_2$ by a spectrometer 17 using a multichannel photomultiplier tube (PMT) as the detector 16 and detecting the light to be detected $L_2$ for every wavelength is shown.

A parameter for analysis of optical property of fine particles may be scattered light, such as forward scattered light for measuring the size of a fine particle or side scattered light, fluorescent light, and Rayleigh scattering or Mie scattering for measuring the structure according to a fine particle to be measured and the purpose of measurement. In addition, fluorescence may be coherent fluorescence or may be incoherent fluorescence.

In addition, a constituent element for performing sorting (splitting) of fine particles based on a measurement result, which is disclosed in JP-T-2005-538727, may be provided in the fine particle measuring apparatus 1. Although a detailed explanation is omitted herein, a fluidic channel for splitting is provided to communicate with the sample fluidic channel 111 in order to sort and recover a fine particle having a desired optical property from fine particles flowing through the sample fluidic channel 111 in the case of performing splitting. In addition, a driving member (actuator) for controlling the flow direction of fine particles in a connecting portion between the sample fluidic channel 111 and the fluidic channel for splitting is provided on the substrate 11. The splitting is performed by controlling the driving member on the basis of a splitting signal from the analysis section.

In addition to the above configuration, the fine particle measuring apparatus 1 according to the embodiment of the present invention includes a light control section 18 that controls the timing of emission of the measurement light $L_1$ to the sample fluidic channel 111. The light control section 18 controls the emission timing of the measurement light $L_1$ scanned and irradiated to each fluidic channel 111 by controlling the laser light source 12 on the basis of an electric signal output from the detector 16. In addition, although the analysis section and the light control section 18 are described as separate members, it is needless to say that the analysis section and the light control section 18 may be formed as one member.

Figure 2:
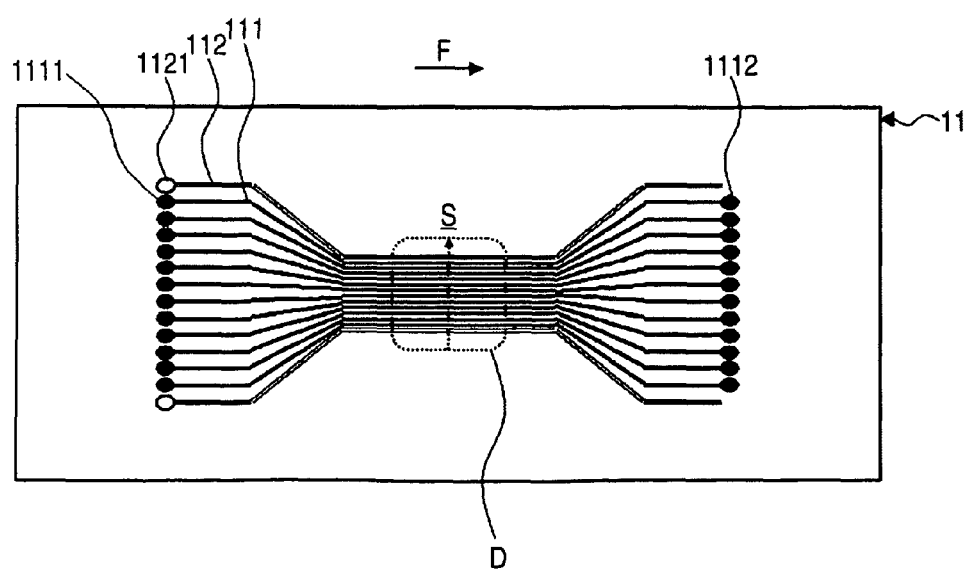
FIG. 2 is a schematic view (top view) illustrating the configuration of a substrate according to the embodiment of the present invention.

FIG. 2 is a schematic view (top view) illustrating the configuration of the substrate 11 according to the embodiment of the present invention.

On the substrate denoted by reference numeral 11, the sample fluidic channels 111 into which fine particles are introduced are provided at predetermined distances. In FIGS. 1 and 2, a case where total twelve sample fluidic channels 111 are provided on the substrate 11 is illustrated. However, the number of sample fluidic channels 111 provided may be any number of two or more.

The substrate 11 is formed of a material which allows the measurement light $L_1$ to be transmitted therethrough and has low wavelength dispersion and small optical error with respect to the measurement light $L_1$, like glass or various kinds of plastics (PP, PC, COP, PDMS).

When glass is used as a material of the substrate 11, fluidic channels (sample fluidic channels 111 and reference fluidic channels 112 to be described later) are transferred by wet etching or dry etching. In addition, when plastic is used as a material of the substrate 11, the fluidic channels are formed by nano imprinting or molding. Thus, fluidic channels having a uniform width may be formed at predetermined distances with the accuracy of 5 μm or less error.

A dispersion solvent containing fine particles to be measured is introduced from a sample inlet 1111, which is provided at one end of the sample fluidic channel 111, into each sample fluidic channel 111.

In this case, the fine particles may be arrayed one by one within the sample fluidic channels 111 by a flow system (not shown). The flow system is configured to include a nozzle used to send out the dispersion solvent containing fine particles as a laminar flow and a nozzle used to send out only a solvent as a laminar flow. By these two nozzles, the laminar flow of the dispersion solvent is generated in the middle of the laminar solvent flow (sheath flow). Furthermore, the fine particles are arrayed one by one in the laminar flow by applying a small pressure difference to the nozzles when sending out the dispersion solvent containing fine particles. Thus, the optical measurement can be performed by irradiating the measurement light $L_1$ onto the fine particles arrayed one by one in the middle of the sample fluidic channels 111.

The fine particle introduced into the sample fluidic channel 111 flows through the sample fluidic channel 111 in a direction indicated by arrow F in the drawing, and the measurement light $L_1$ is irradiated in a detection region D (refer to a dotted line in the drawing). After irradiation, the fine particle is made to further flow in the direction indicated by arrow F and is then discharged outside the substrate 11 from a sample outlet 1112 provided at the other end of the sample fluidic channel 111.

Irradiation of the measurement light $L_1$ is performed by causing the scanning section 13 to scan the measurement light $L_1$, which is emitted from the laser light source 12, to each sample fluidic channel 111 (refer to FIG. 1). In FIG. 2, a dotted arrow S indicates a scanning line of the measurement light $L_1$. An explanation will be made assuming that the measurement light $L_1$ is scanned upward from below of the substrate 11 in FIG. 2. In addition, the scanning does not need to be performed in one direction on the scanning line S, but may be performed in a bidirectional (round trip) way.

In the substrate 11, the reference fluidic channels 112 are provided at outer sides of the sample fluidic channels 111 in order to make it possible to emit the measurement light $L_1$ to the sample fluidic channels 111 at a proper timing in scanning of the measurement light $L_1$.

The reference fluidic channels 112 are provided at both ends of the sample fluidic channels 111 in the scanning direction S of the measurement light $L_1$, and an arrangement distance between each of the reference fluidic channels 112 and the sample fluidic channel 111 adjacent thereto is equal to the predetermined distance between the sample fluidic channels 111.

Fine particles for reference and/or a fluorescent material for reference are introduced into the reference fluidic channels 112. The fine particle for reference and the fluorescent material for reference are not particularly restricted as long as they can change the optical property of the measurement light $L_1$ when the measurement light $L_1$ is irradiated, and a micro bead or fluorescent dye typically used may be used. Here, the "change of optical property" includes a wavelength change, a deflection change, and an intensity change caused by diffusion, diffraction, deflection, absorption, and the like of the measurement light $L_1$. In a broad sense, the "change of optical property" further includes a change in which irradiated light is absorbed to emit fluorescent light with a different wavelength.

For example, when microbeads are introduced as fine particles for reference into the reference fluidic channels 112, the optical property of the measurement light $L_1$ changes by diffusion caused by the microbeads. In addition, when a fluorescent material having a wavelength of the measurement light $L_1$ as an excitation wavelength is introduced as a fluorescent material for reference into the reference fluidic channels 112, fluorescent light having a different wavelength (emission wavelength) is generated by irradiation of the measurement light $L_1$.

A dispersion solvent containing fine particles for reference or/and a solution containing a fluorescent material for reference is introduced from a reference material inlet 1121 provided at one end of the reference fluidic channel 112 into the reference fluidic channel 112. The introduction may be performed continuously during the measurement by discharging the solvent or solution sent to the outside of the substrate 11 through a reference material outlet (not shown) provided at the other end. In addition, as shown in FIG. 2, the other end of the reference fluidic channel 112 may be blocked and a solvent or a solution may be injected and filled once.

In addition, the fine particles for reference and the fluorescent material for reference may be introduced into the reference fluidic channels 112 beforehand. For example, the fine particles for reference and the fluorescent material for reference may be filled within the reference fluidic channels 112 in manufacturing the substrate 11 without providing the reference material inlet 1121. In addition, a single material or a plurality of materials combined may be used as each of the fine particle for reference and the fluorescent material for reference, and both the fine particle for reference and the fluorescent material for reference may be introduced into the reference fluidic channel 112.

Such a change of optical property of the measurement light $L_1$ caused by the fine particle for reference or/and the fluorescent material for reference can be detected by the same detection system as for the light to be detected $L_2$ generated from the fine particle in the sample fluidic channel 111.

Specifically, light generated by irradiation of the measurement light $L_1$ onto the fine particle for reference or/and the fluorescent material for reference is condensed by the objective lens 14, passes through the scanning section 13 and the spectrometer 17, is detected by the detector 16, and is converted into an electric signal (refer to FIG. 1).

Then, the light control section 18 controls the timing of emission of the measurement light $L_1$ to the sample fluidic channel 111 by receiving an output of the electric signal, detecting a change of optical property of the measurement light $L_1$, and controlling the laser light source 12.

As parameters for detecting the change of optical property, a wavelength, a deflection angle, strength, and the like are set according to a fine particle for reference and a fluorescent material for reference to be used. For example, diffusion caused by a microbead is detected in the above example in which the microbead is used as a fine particle for reference. In addition, in a case where a fluorescent material for reference is used, detection of fluorescence light corresponding to an emission wavelength is performed.

Hereinafter, a control of emission timing of the measurement light $L_1$ using the light control section 18 will be specifically described.

Figure 3:
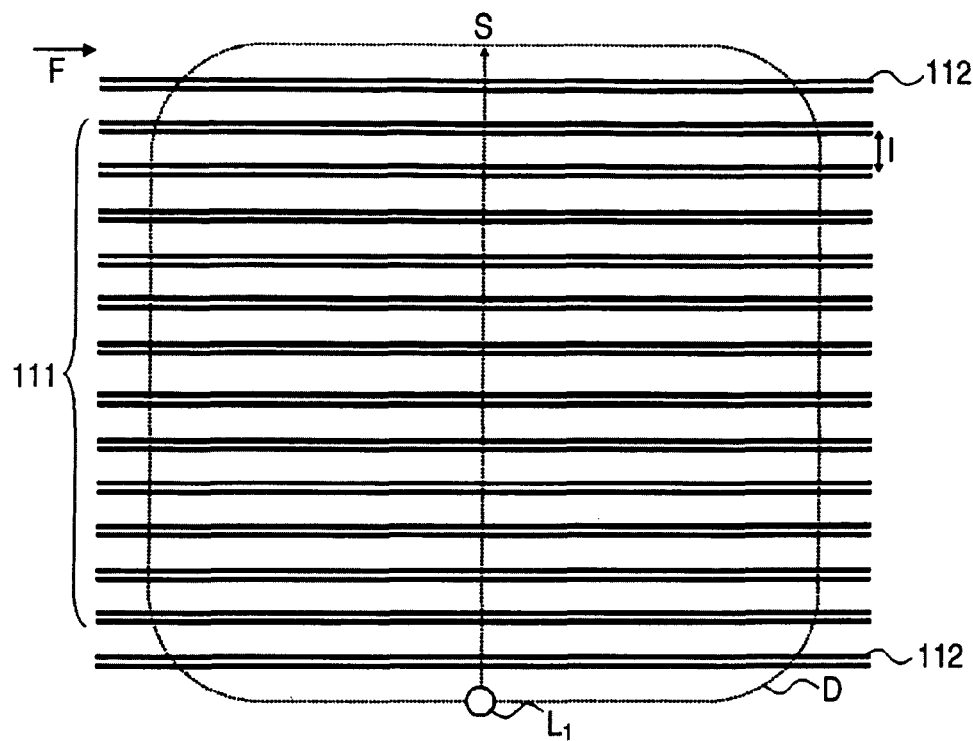
FIG. 3 is an enlarged view (top view) schematically illustrating a detection region of the substrate.

FIG. 3 is an enlarged view (top view) schematically illustrating the detection region D of the substrate 11.

In the drawing, the reference numeral $L_1$ indicates a laser spot of the measurement light $L_1$ on an imaging surface on the sample fluidic channel 111 (reaction region D). The measurement light $L_1$ is scanned on the scanning line S upward from a lower side in the drawing and is irradiated to the reference fluidic channel 112, each sample fluidic channel 111, and the reference fluidic channel 112.

The sample fluidic channels 111 and the reference fluidic channels 112 are arrayed at predetermined distances denoted by reference numeral 1 in the drawing.

Fine particles for reference or/and a fluorescent material for reference are introduced into the reference fluidic channels 112, and the optical property of the measurement light $L_1$ changes by the fine particles for reference or/and the fluorescent material for reference when the measurement light $L_1$ is irradiated to the reference fluidic channels 112.

The light control section 18 calculates a time T required for the measurement light $L_1$ to be scanned between the reference fluidic channels 112 by detecting the change of optical property from the electric signal transmitted from the detector 16.

Specifically, assuming that a time when a change of optical property caused by one reference fluidic channel 112 is detected is time 0, the time T until a change of optical property caused by another reference fluidic channel 112 is detected is acquired. In FIG. 3, a time when a change of optical property caused by a reference fluidic channel, which is located at a lower side in the drawing, is detected is the time 0 and a time when the same change caused by an upper reference fluidic channel is detected is the time T.

Then, the light control section 18 calculates the emission timing of the measurement light $L_1$ on the basis of the following expression (1) using the acquired time T.

$$tk = 0 + k \times T/(m+1) \qquad (1)$$

Here, "m" denotes the number of sample fluidic channels 111 and "tk" denotes a time of emission of the measurement light $L_1$ to the sample fluidic channel 111 to which the measurement light $L_1$ is irradiated for the k-th time. In addition, the number m of sample fluidic channels 111 may be set and stored beforehand in the light control section 18 of the measuring apparatus 1 according to the substrate 11 to be used.

Specifically, in FIG. 3 (the number m of sample fluidic channels 111 is 12), the measurement light $L_1$ is emitted at time T/13, 2T/13, 3T/13, 4T/13, 5T/13, 6T/13, 7T/13, 8T/13, 9T/13, 10T/13, 11T/13, and 12T/13 sequentially from the sample fluidic channel 111 located at the lower side in the drawing. The emission time of the measurement light $L_1$ at each time is a very short time, for example, about 1 μs.

Since the sample fluidic channels 111 and the reference fluidic channels 112 are arrayed at predetermined equal distances 1 as described above, each time calculated may be considered as a time at which the center of a laser spot of the measurement light $L_1$ coincides with the middle of each sample fluidic channel 111 in the width direction thereof.

Thus, by emitting the measurement light $L_1$ at the timing, the measurement light $L_1$ can be irradiated to each sample fluidic channel 111 at a proper timing without performing unnecessary irradiation of the measurement light $L_1$ in a case where a laser spot is located in a land (region between fluidic channels of the substrate) or a case where the center of the laser spot deviates from the middle of the sample fluidic channel 111.

Thus, in the fine particle measuring apparatus 1 according to the embodiment of the present invention, the timing of emission of the measurement light $L_1$ to each sample fluidic channel 111 can be controlled by detecting a change of optical property of the measurement light $L_1$ caused by the reference fluidic channels provided on the substrate. Accordingly, even if a position of the substrate 11 attached to the fine particle measuring apparatus 1 deviates, it is possible to obtain the high measurement accuracy by irradiating the measurement light $L_1$ to each sample fluidic channel 111 at a proper timing.

Figure 4:
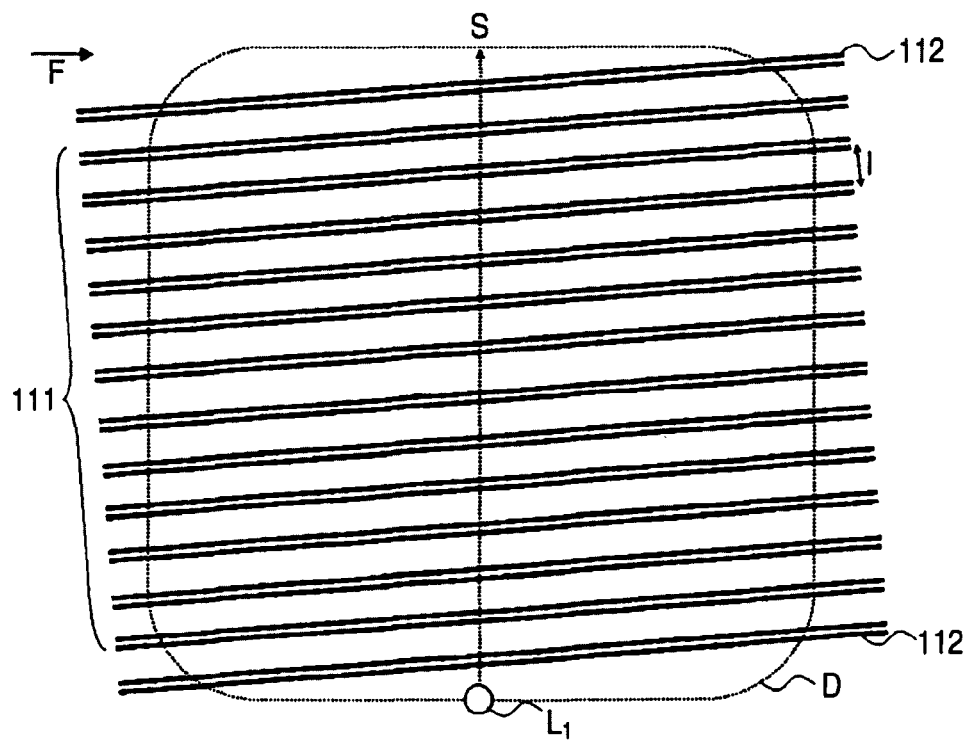
FIG. 4 is an enlarged view (top view) schematically illustrating a detection region of a substrate attached in a state where sample fluidic channels and reference fluidic channels are attached to be inclined from a scanning line of measurement light without crossing at right angles.

FIG. 4 shows the substrate 11 in a state where the sample fluidic channels 111 and the reference fluidic channels 112 are attached to be inclined from the scanning line S of the measurement light $L_1$ without crossing at right angles. FIG. 4 is an enlarged view schematically illustrating the detection region D.

As described above, fluidic channels on the substrate can be formed at equal distances with the accuracy of 5 μm or less error by etching, nanoimprinting, and the like. For this reason, as long as substrates designed to have the same size, the same width or number of fluidic channels, and the like are used, the timing of irradiation of measurement light to sample fluidic channels on the substrate can be uniquely determined. In this case, however, when the attaching position of the substrate deviates as shown in FIG. 4, measurement light may not be irradiated to the sample fluidic channels at proper timing. As a result, an accurate measurement result may not be obtained.

On the other hand, in the fine particle measuring apparatus 1 according to the embodiment of the present invention, even if the sample fluidic channels 111 and the reference fluidic channels 112 are attached to deviate in the vertical direction or to be inclined from the scanning line S as shown in FIG. 4, the measurement light $L_1$ can be irradiated at a proper timing by calculating the emission timing of the measurement light $L_1$ on the basis of the time T required for the measurement light $L_1$ to be scanned between the reference fluidic channels 112.

Furthermore, in the fine particle measuring apparatus 1 according to the embodiment of the present invention, the unnecessary measurement light $L_1$ is not irradiated in a case where a laser spot is located in a land or a case where the center of the laser spot deviates from the middle of the sample fluidic channel 111. As a result, when the measurement is performed by irradiating a plurality of measurement light beams to the sample fluidic channels 111, high measurement sensitivity can be obtained by suppressing the interference (crosstalk) between light beams.

Figure 5:
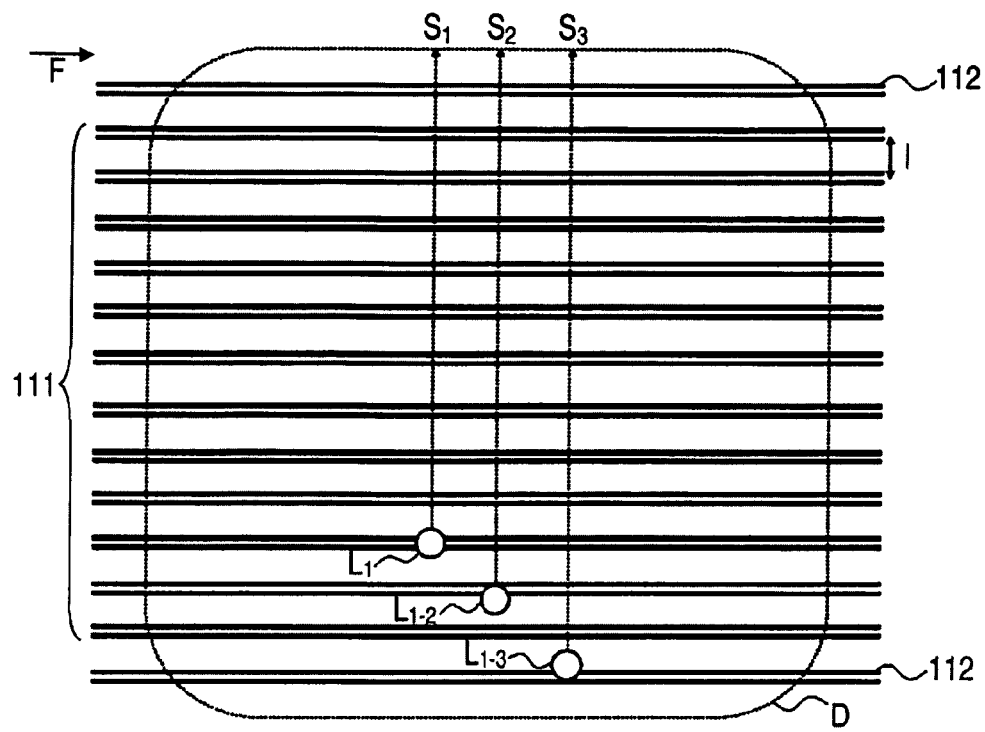
FIG. 5 is an enlarged view (top view) schematically illustrating a detection region of a substrate in a case where measurement is performed by irradiating measurement light beams to sample fluidic channels.

FIG. 5 is an enlarged view schematically illustrating the detection region D in performing measurement by irradiating a plurality of measurement light beams to the sample fluidic channels 111. In the drawing, reference numerals $L_1$, $L_{1-2}$, and $L_{1-3}$ indicate laser spots of each measurement light on an imaging surface on the sample fluidic channel 111 (reaction region D).

For example, in case of measuring a fluorescent characteristic of fine particles marked by a plurality of fluorescent dye, a plurality of measurement light beams is irradiated onto the fine particles by using a plurality of laser light sources that emit light having a wavelength corresponding to an excitation wavelength of each fluorescent dye. Although a case where the three measurement light beams $L_1$, $L_{1-2}$, and $L_{1-3}$ are used is shown in FIG. 5, the number of measurement light beams may be arbitrarily set as needed. The measurement light beams $L_1$, $L_{1-2}$, and $L_{1-3}$ may have wavelengths of 405 nm, 473 nm, and 658 nm, respectively, for example.

The measurement light beams $L_1$, $L_{1-2}$, and $L_{1-3}$ are scanned through scanning lines $S_1$, $S_2$, and $S_3$, respectively, and are irradiated to the sample fluidic channels 111. The measurement light beams $L_{1-2}$ and $L_{1-3}$ may be scanned together with the measurement light beam $L_1$ by means of the scanning section 13 shown in FIG. 1, which scans light from each laser light source. Alternatively, the measurement light beams $L_{1-2}$ and $L_{1-3}$ may be scanned by a separate scanning section provided for the measurement light beams $L_{1-2}$ and $L_{1-3}$. In order to make the configuration of the apparatus simple, it is preferable to scan the measurement light beams $L_1$, $L_{1-2}$, and $L_{1-3}$ together by the same scanning section.

In case of performing measurement by scanning the three measurement light beams $L_1$, $L_{1-2}$, and $L_{1-3}$ as described above, when light beams to be detected are simultaneously generated from the different sample fluidic channel 111 by irradiation of each measurement light, a noise may be generated due to crosstalk between the light beams to be detected. This may lower the measurement sensitivity.

For example, when all of the measurement light beams $L_1$, $L_{1-2}$, and $L_{1-3}$ are emitted in a case where the measurement light beams $L_1$, $L_{1-2}$, and $L_{1-3}$ are scanned from the positions shown in FIG. 5, light beams to be detected $L_2$, $L_{2-2}$, and $L_{2-3}$ are generated from fine particles in the sample fluidic channels 111 to which the measurement light beams are irradiated, respectively. As a result, crosstalk between the light beams to be measured occurs.

In order to avoid the crosstalk, light to be detected, which is generated from each sample fluidic channel 111, needs to be detected by an individual detector. In this case, however, a problem in terms of manufacturing cost occurs because the configuration of the apparatus becomes complicated.

Therefore, as long as light to be detected can be generated from fine particles and the generated light to be detected can be detected, it is preferable to avoid that light beams to be measured are simultaneously generated from the different sample fluidic channels 111 by shortening the emission time of each of the measurement light beams $L_1$, $L_{1-2}$, and $L_{1-3}$.

In the fine particle measuring apparatus 1 according to the embodiment of the present invention, measurement light is emitted at timing when the center of a laser spot of the measurement light coincides with the middle of each sample fluidic channel 111 in a width direction thereof. For example, in FIG. 5, only the measurement light beam $L_1$ the center of a laser spot of which is located in the middle of the sample fluidic channel 111 in the width direction is emitted, and the measurement light beams $L_{1-2}$ and $L_{1-3}$ the centers of laser spots of which deviate from the middle of the sample fluidic channel 111 are not emitted.

Thus, in the fine particle measuring apparatus 1, it is possible to avoid that light beams to be measured are simultaneously generated from the different sample fluidic channels 111 and to suppress occurrence of crosstalk between the light beams to be measured. As a result, the high measurement sensitivity can be obtained.

Furthermore, in case of scanning the measurement light beams $L_1$, $L_{1-2}$, and $L_{1-3}$ having different wavelengths by scanning sections separately provided, it is necessary to introduce fine particles for reference or/and a fluorescent material for reference, which can cause the change of different optical property for every wavelength, into the reference fluidic channels 112 in order to separately detect the characteristic change of each measurement light beam in the light control section 18 and to control each emission timing.

Figure 6:
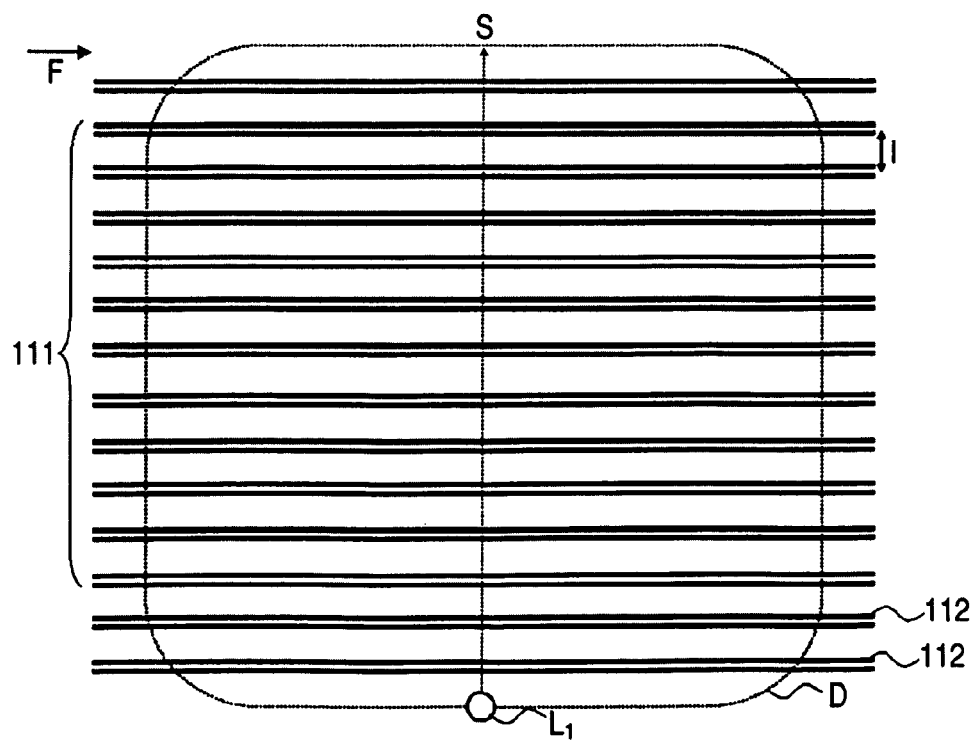
FIG. 6 is an enlarged view (top view) schematically illustrating a detection region of a substrate according to another embodiment.

FIG. 6 is an enlarged view (top view) schematically illustrating the detection region D of the substrate 11 according to another embodiment.

In FIG. 6, the reference numeral $L_1$ indicates a laser spot of the measurement light $L_1$ on an imaging surface on the sample fluidic channel 111 (reaction region D). Similar to FIG. 3, the sample fluidic channels 111 and the reference fluidic channels 112 are arrayed at predetermined distances denoted by reference numeral 1 in the drawing.

However, in FIG. 6, the reference fluidic channels 112 are disposed on each one sides of the sample fluidic channels 111 in the scanning direction S of the measurement light $L_1$ so as to be adjacent to each other.

In this case, the light control section 18 calculates the emission timing of the measurement light $L_1$ on the basis of the following expression (2) using the acquired time T.

$$tk=0+(k+1)\times T/(m+1) \quad (2)$$

Here, "m" denotes the number of sample fluidic channels 111 and "tk" denotes a time of emission of the measurement light $L_1$ to the sample fluidic channel 111 to which the measurement light $L_1$ is irradiated for the k-th time.

As described earlier, in a case where the light control section 18 detects and calculates a change of optical property caused by the reference fluidic channels 112 using an electric signal from the detector 16, assuming that a time when a change of optical property caused by one reference fluidic channel 112 is detected is time 0, the time T indicates a time until a change of optical property caused by another reference fluidic channel 112 is detected. That is, the time T is equivalent to a time required for the measurement light $L_1$ to be scanned between the reference fluidic channels 112.

Specifically, in FIG. 6 (the number m of sample fluidic channels 111 is 12), time when the measurement light $L_1$ is emitted to each sample fluidic channel 111 is time 2T/13, 3T/13, 4T/13, 5T/13, 6T/13, 7T/13, 8T/13, 9T/13, 10T/13, 11T/13, 12T/13, and 13T/13 sequentially from the sample fluidic channel 111 located at a lower side in the drawing.

Thus, the arrangement positions of the reference fluidic channels 112 may be arbitrarily set in a condition that the reference fluidic channels 112 are arranged at the predetermined distances 1 along the scanning direction S of the measurement light $L_1$. In this case, by properly modifying the calculating expressions (expressions (1) and (2)) of emission timing according to the arrangement positions of the reference fluidic channels 112, it is possible to emit the measurement light $L_1$ at timing when the center of a laser spot of the measurement light $L_1$ coincides with the middle of each sample fluidic channel 111 in the width direction.

In addition, the number of reference fluidic channels 112 does not always need to be two. For example, three or more reference fluidic channels 112 may also be used. Also in this case, the calculating expressions (expressions (1) and (2)) of emission timing are preferably modified according to the arrangement positions and number of the reference fluidic channels 112.

Figure 7:
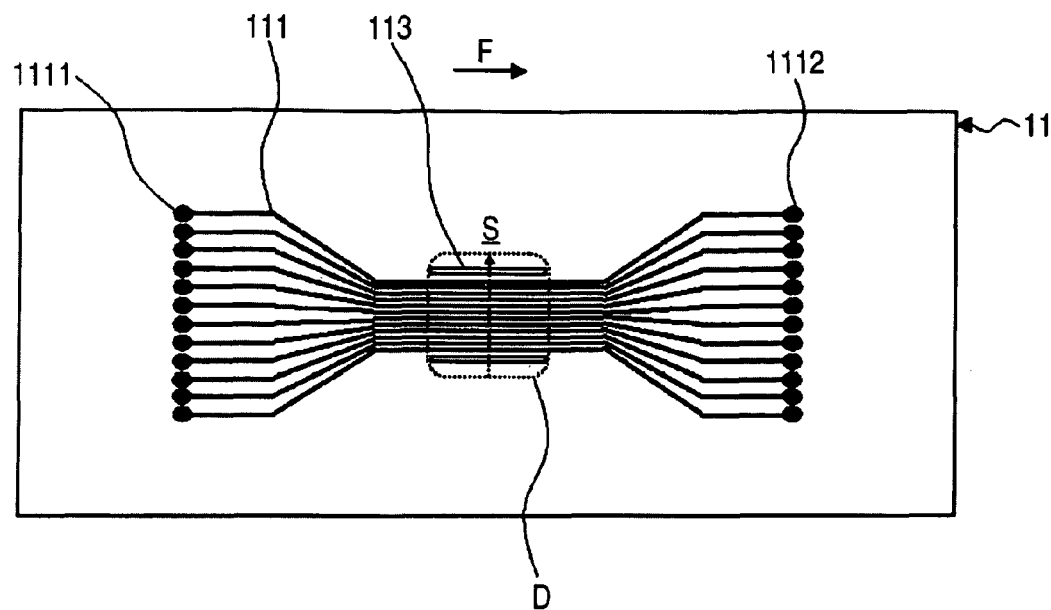
FIG. 7 is a schematic view (top view) illustrating the configuration of the substrate according to another embodiment.
Figure 8:
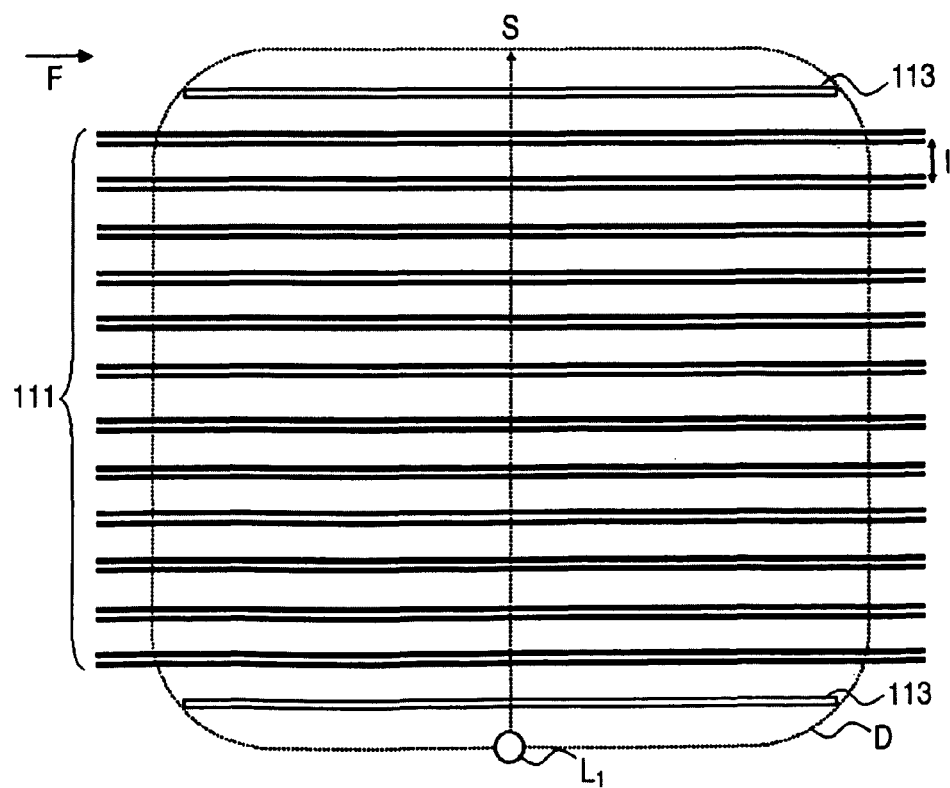
FIG. 8 is an enlarged view (top view) schematically illustrating a detection region of the substrate shown in FIG. 7.

FIG. 7 is a schematic view (top view) illustrating the configuration of the substrate 11 according to another embodiment. FIG. 8 is an enlarged view (top view) schematically illustrating the detection region D of the substrate 11.

Similar to FIG. 2, the sample fluidic channels 111 are provided at the predetermined distances 1 (refer to FIG. 8) on the substrate denoted by reference numeral 11. A method of introducing a fine particle into the sample fluidic channel 111, the scanning direction S of the measurement light $L_1$, and the like are similar to those described in FIG. 2.

In FIG. 7, however, instead of the reference fluidic channels 112, reference regions 113 are provided at outer sides of the sample fluidic channels 111 as a configuration for emitting the measurement light $L_1$ to each sample fluidic channel 111 at a proper timing in scanning of the measurement light $L_1$.

The reference regions 113 are provided at both ends of the sample fluidic channels 111 in the scanning direction S of the measurement light $L_1$, and an arrangement distance between each of the reference regions 113 and the sample fluidic channel 111 adjacent thereto is equal to the predetermined distance 1 (refer to FIG. 8) between the sample fluidic channels 111.

Similar to the reference fluidic channels 112, the reference regions 113 are regions where not only a wavelength change, a deflection change, and an intensity change caused by diffusion, diffraction, deflection, absorption, and the like of the measurement light $L_1$ but also a change in which irradiated light is absorbed to emit fluorescent light with a different wavelength may occur by irradiating the measurement light $L_1$.

Such a region where the change of optical property of the measurement light $L_1$ can be caused may be formed by fixing a material, which is able to diffuse, diffract, deflect, and absorb the measurement light $L_1$, on a surface of the substrate 11. For example, the region is formed by using a method of forming a metal film or a dielectric film by sputtering or vapor deposition, or a method of fixing a fluorescent material or a coloring material.

Alternatively, the region may also be formed by a fine structure of the surface of the substrate 11. The fine structure is formed by a fine groove of the substrate surface or pit embedding. In this case, it is useful to perform the measurement by making the scanning sections separately provided scan a plurality of measurement light beams with different wavelengths, as described particularly in FIG. 5, because measurement light given a different angle of reflection or angle of transmission diffraction corresponding to the wavelength, whereby a characteristic change of each measurement light beam can be detected individually.

The metal film, the dielectric film, and the fine structure may also be formed by patterning. Accordingly, even if a chip is dirty, a plurality of signal patterns are obtained since a plurality of patterns are provided. As a result, error correction used for an optical disk or the like becomes possible or an address capable of specifying a more accurate position may be replaced.

The point that the arrangement positions and number of reference regions 113 may be arbitrarily set in a condition that the reference regions 113 are arranged at the predetermined distances 1 along the scanning direction S of the measurement light $L_1$ is similar to that described for the reference fluidic channels 112. In this case, by properly modifying the calculating expressions (expressions (1) and (2)) of emission timing according to the arrangement positions and the number, it is possible to emit the measurement light $L_1$ at a proper timing.

Figure 9:
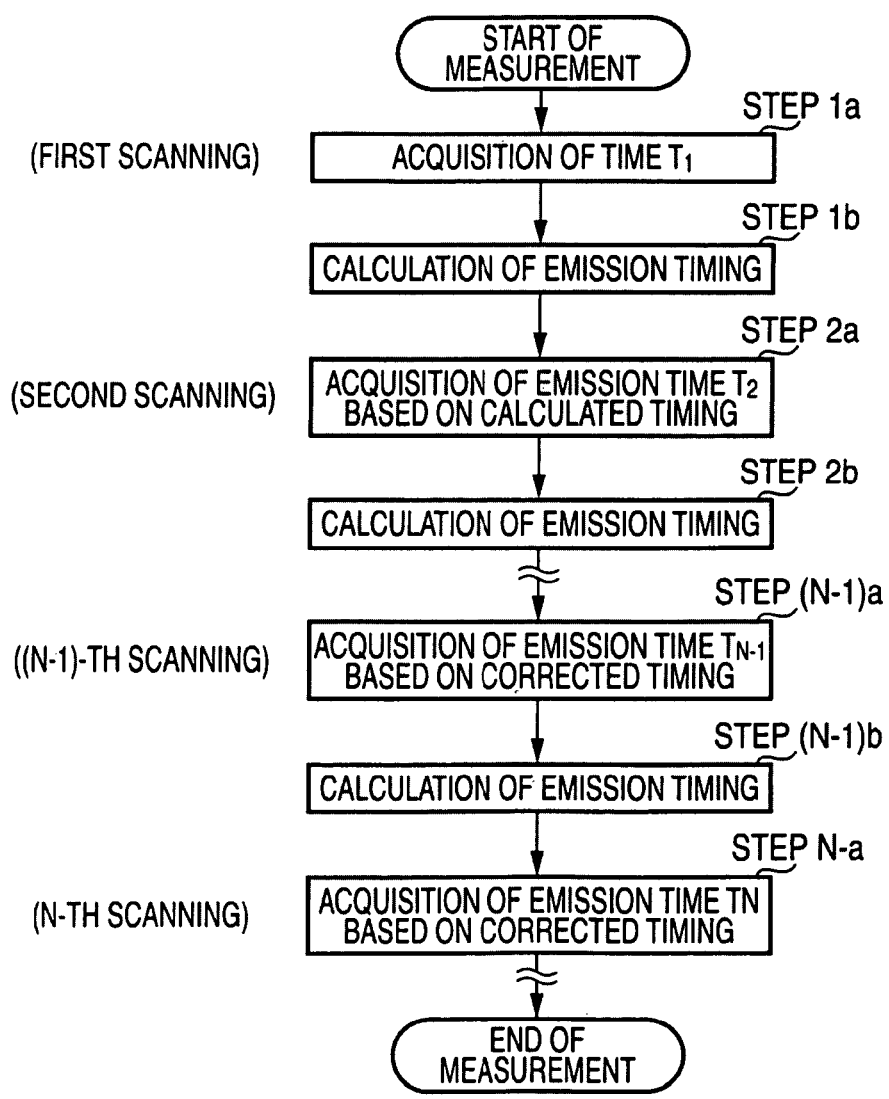
FIG. 9 is a flow chart illustrating a control procedure of emission timing of measurement light using a light control section.

Next, a control procedure of the emission timing of the measurement light $L_1$ using the light control section 18 will be described on the basis of a flow chart shown in FIG. 9 while referring to the example of FIG. 3.

First, in first scanning after the start of measurement, the measurement light $L_1$ is scanned to acquire the irradiation timing of the measurement light $L_1$ (step 1a). In this case, it is preferable not to detect light to be detected $L_2$ which is generated from a fine particle by irradiation of the measurement light $L_1$.

In this first scanning (step 1a), the light control section 18 makes the measurement light $L_1$ emitted continuously. As a result, the measurement light $L_1$ is sequentially irradiated in the order of the reference fluidic channel 112, each sample fluidic channel 111, and the reference fluidic channel 112 upward from the lower side of FIG. 3.

The light control section 18 detects a change of optical property of the measurement light $L_1$ caused by irradiation of the measurement light $L_1$ to the reference fluidic channels 112 and acquires a time $T_1$ required for the measurement light $L_1$ to be scanned between the reference fluidic channels 112. In FIG. 3, assuming that a time when the change of optical property caused by the lower reference fluidic channel 112 is detected is time 0, a time when the same change caused by the upper reference fluidic channel 112 is detected is the time $T_1$.

Then, in step 1b, the light control section 18 calculates the emission timing of the measurement light $L_1$ on the basis of the following expression (1) using the acquired time $T_1$.

$$tk = 0 + k \times T/(m+1) \quad (1)$$

Here, "m" denotes the number of sample fluidic channels 111 and "tk" denotes a time of emission of the measurement light $L_1$ to the sample fluidic channel 111 to which the measurement light $L_1$ is irradiated for the k-th time.

Then, in second scanning, the light control section 18 makes the measurement light $L_1$ emitted at each acquired time by newly setting a time when the optical property change, which is caused by the reference fluidic channel 112 located at a lower side of FIG. 3, is detected as time 0 (step 2a).

Specifically, in FIG. 3 (the number m of sample fluidic channels 111 is 12), the measurement light $L_1$ is emitted at time $T_1/13, 2T_1/13, 3T_1/13, 4T_1/13, 5T_1/13, 6T_1/13, 7T_1/13, 8T_1/13, 9T_1/13, 10T_1/13, 11T_1/13$, and $12T_1/13$ sequentially from the lower sample fluidic channel 111. Thus, the measurement of a fine particle in each sample fluidic channel 111 is performed.

In order to acquire the time 0 in second scanning, the light control section 18 maintains emission of the measurement light $L_1$ at the start of second scanning after the first scanning ends. Then, after the measurement light $L_1$ is irradiated to the lower reference fluidic channel 112 and the change of optical property is detected to thereby acquire the time 0, the light control section 18 performs the second scanning by making the measurement light $L_1$ emitted only at each time described above.

In addition, the light control section 18 acquires a time $T_2$, which is required for the measurement light $L_1$ to be scanned between the reference fluidic channels 112, in the second scanning (step 2a).

For this reason, the light control section 18 maintains emission of the measurement light $L_1$ after emitting the measurement light $L_1$ to the last sample fluidic channel 111 at the time $12T_1/13$. Thus, the light control section 18 detects the change of optical property occurring when the measurement light $L_1$ is irradiated to the upper reference fluidic channel 112 and acquires the time $T_2$.

Subsequently, the light control section 18 similarly calculates the emission timing of the measurement light $L_1$ for N-th scanning (step (N−1)b) on the basis of time $T_{N-1}$ acquired in (N−1)-th scanning (step (N−1)a) and performs N-th scanning according to the calculated emission timing (step Na).

Thus, in the fine particle measuring apparatus 1, it is possible to perform scanning in a state where the measurement light $L_1$ is emitted at every timing when the center of a laser spot of the measurement light $L_1$ coincides with the middle of each sample fluidic channel 111 in the width direction by controlling the emission timing of the measurement light $L_1$ for every scanning.

This is particularly effective in a case where deviation occurs in a scanning period of the measurement light $L_1$. As described above in FIG. 1, the measurement light $L_1$ is scanned to the sample fluidic channels 111 by the scanning section 13 which includes a dichroic mirror or a polygon mirror, a galvano mirror, an acousto-optic element, an electro-optic element, and the like and is disposed on the optical path of the measurement light $L_1$ emitted from the laser light source 12. Scanning may be performed in a period of about 1 kHz in the case of the dichroic mirror and about 20 kHz in the case of a tetracosahedral polygon mirror. Even though the scanning period of each may be controlled with high precision, it is technically difficult to maintain a perfect fixed period due to the instability of a driving device.

Accordingly, in case of irradiating the measurement light $L_1$ to each sample fluidic channel 111 at the emission timing set beforehand as a fixed value, when deviation occurs in a scanning period of the scanning section 13 during measurement, the measurement light $L_1$ is emitted at an improper timing when the laser spot of the measurement light $L_1$ is located at a land (region between fluidic channels of the substrate) or at a position deviating from the middle of the sample fluidic channel 111, therefore an accurate measurement result may not be obtained.

On the other hand, in the fine particle measuring apparatus 1 according to the embodiment of the present invention, the light control section 18 controls the timing of emission of the measurement light $L_1$ to each sample fluidic channel 111 in N-th scanning on the basis of the time $T_{N-1}$ acquired in (N−1)-th scanning. Accordingly, even if deviation occurs in the scanning period of the scanning section 13 during measurement, the measurement light $L_1$ can be emitted all the time in a condition where the center of the laser spot of the measurement light $L_1$ coincides with the middle of each sample fluidic channel 111 in the width direction. As a result, an accurate measurement result can be obtained.

Although the control procedure of emission timing of the measurement light $L_1$ using the light control section 18 has been described using the substrate 11 shown in FIG. 3 as an example, the same control may also be made for the substrate 11 according to another embodiment shown in FIG. 6.

The fine particle measuring method according to the embodiment of the present invention may be used for optical measurement of biological fine particles, such as cells, microorganisms, and liposomes, or synthetic particles, such as latex particles, gel particles, and industrial particles.

It should be understood by those skilled in the art that various modifications, combinations, sub-combinations and alterations may occur depending on design requirements and other factors insofar as they are within the scope of the appended claims or the equivalents thereof.

What is claimed is:

1. A fine particle measuring method for performing optical measurement of fine particles introduced into a plurality of sample fluidic channels provided at predetermined equal distances on a substrate by scanning a measurement light to the plurality of sample fluidic channels, the method comprising the steps of:

sequentially irradiating the measurement light to at least two or more reference regions provided on the substrate on one or two outer sides of the plurality of sample fluidic channels;

detecting a change of an optical property occurring in the measurement light due to the reference regions;

calculating a time for emitting the measurement light to each of the plurality of sample fluidic channels respectively on the basis of a time difference between a detection time of a change of the optical property caused by one of the at least two or more reference regions and a detection time of a change of the optical property caused by another one of the at least two or more reference regions and a total number of the plurality of sample fluidic channels;

scanning the measurement light to each of the plurality of sample fluidic channels at the calculated respective time, wherein a light is generated from a fine particle in each of the plurality of sample fluidic channels;

converting the light generated from the fine particle into an electric signal; and analyzing an optical property of the fine particle based on the electric signal to output a measurement result.

2. The fine particle measuring method according to claim 1, wherein the at least two or more reference regions are reference fluidic channels into which fine particles for reference or/and a fluorescent material for reference are introduced, and the change of the optical property is caused by the fine particles for reference or/and the fluorescent material for reference.

3. A fine particle measuring apparatus for performing optical measurement of fine particles introduced into a plurality of sample fluidic channels provided at predetermined equal distances on a substrate by scanning a measurement light to the plurality of sample fluidic channels, the apparatus comprising:

a light irradiating section that sequentially irradiates the measurement light to at least two or more reference regions provided on the substrate on one or two outer sides of the plurality of sample fluidic channels;

a light detecting section that detects a change of an optical property occurring in the measurement light due to the reference regions;

a light control section that:

calculates a time for emitting the measurement light to each of the plurality of sample fluidic channels respectively on the basis of a time difference between a detection time of a change of the optical property caused by one of the at least two or more reference regions and a detection time of a change of the optical property caused by another one of the at least two or more reference regions and a total number of sample fluidic channels, and scans the measurement light to each of the plurality of sample fluidic channels at the calculated respective time, wherein a light is generated from a fine particle in each of the plurality of sample fluidic channels and is converted into an electric signal by the light detecting section; and an analysis section that analyzes an optical property of the fine particle based on the electric signal and outputs a measurement result.

* * * * *